(12) United States Patent
Bastuck et al.

(10) Patent No.: US 6,692,946 B2
(45) Date of Patent: Feb. 17, 2004

(54) POLYNUCLEOTIDES ENCODING THE NADA GENE AND METHODS OF PRODUCING NICOTINIC ACID OR NICOTINIC ACID DERIVATIVES

(75) Inventors: Christine Bastuck, Bielefeld (DE); Brigitte Bathe, Salzkotten (DE); Nicole Dusch, Bielefeld (DE); Bettina Moeckel, Duesseldorf (DE); Georg Thierbach, Bielefeld (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/789,599

(22) Filed: Feb. 22, 2001

(65) Prior Publication Data

US 2002/0137163 A1 Sep. 26, 2002

(30) Foreign Application Priority Data

Nov. 10, 2000 (DE) .......................................... 100 55 869

(51) Int. Cl.[7] .................................................. C12N 9/04
(52) U.S. Cl. ..................... 435/190; 435/183; 435/189; 435/252.3; 435/252.32; 435/320.1; 536/23.2
(58) Field of Search ................................. 435/183, 189, 435/190, 252.3, 252.32, 320.1; 536/23.2

(56) References Cited

U.S. PATENT DOCUMENTS

| | | |
|---|---|---|
| 3,708,394 A | 1/1973 | Nakayama et al. |
| 5,236,831 A | 8/1993 | Katsumata et al. |

FOREIGN PATENT DOCUMENTS

| | | |
|---|---|---|
| EP | 0 187 680 | 7/1986 |
| EP | 1108790 A2 | 6/2001 |
| EP | 1 108 790 | 6/2001 |
| WO | WO 01/00802 | 1/2001 |
| WO | WO 01/00843 | 1/2001 |
| WO | WO 01/00845 | 1/2001 |
| WO | WO 01/00847 | 1/2001 |

OTHER PUBLICATIONS

Strausberg. Accession A14935922. Mar. 11, 1999.*
Redenbach et al. Accession AL049497. Mar. 24, 1999. (Alignment No. 1).*
Attwood et al. Which craft is best in bioinformatics? Comput. Chem. 2001, vol. 25(4), pp. 329–339.*
Ponting, C.P. Issues in predicting protein function from sequence. Brief. Bioinform. Mar. 2001, vol. 2(1), pp. 19–29.*
F. Fuji, et al., Database Swissprot 'Online!' of Nuecleic Acids Res., vol. 28, Accession No. Q9KDJ3, XP–002193734, pp. 4317–4331, "Complete Genome Sequence of the Alkaliphilic Bacterium *Bacillus Halodurans* and Genomic Sequence Comparison with *Bacillus Subtilis*.", Oct. 1, 2000.
V. Tosato, et al., Database Swissprot 'Online!', Accession No. Q9KWZ1, XP–002193735, "A 17.8 KB Segment in the spoVB–nadC Region of the *Bacillus Subtilis* 168 Chromosome: Sequencing and RUV Operon Identification.", Oct. 1, 2000.
F. Kunst, et al., Database Swissprot 'Online!'of Nature, vol. 390, Accession No. 032063, XP–002193736, pp. 249–256, "The Complete Genome Sequence of the Gram–Positive Bacterium *Bacillus Subtilis*.", Jan. 1, 1998.
Patent Abstracts of Japan, JP 60–133880, Jul. 17, 1985.

* cited by examiner

*Primary Examiner*—Ponnathapu Achutamurthy
*Assistant Examiner*—Christian L. Fronda
(74) *Attorney, Agent, or Firm*—Oblon, Spivak, McClelland, Maier & Neustadt, P.C.

(57) ABSTRACT

The present invention relates to polynucleotides corresponding to the nadA gene and which encode the quinolinate synthetase A protein, methods of producing nicotinic acid or nicotinic acid derivatives, and methods of screening for polynucleotides which encode proteins having quinolinate synthetase A activity.

23 Claims, 1 Drawing Sheet

POLYNUCLEOTIDES ENCODING THE NADA GENE AND METHODS OF PRODUCING NICOTINIC ACID OR NICOTINIC ACID DERIVATIVES

BACKGROUND OF THE INVENTION

1. Field of the Invention

The present invention relates to polynucleotides corresponding to the nadA gene and which encode the quinolinate synthetase A protein, methods of producing nicotinic acid or nicotinic acid derivatives, and methods of screening for polynucleotides which encode proteins having quinolinate synthetase A activity.

2. Discussion of the Background

Nicotinic acid and nicotinic acid derivatives are used in human medicine, in the pharmaceuticals industry, in the foodstuffs industry and in animal nutrition. It is known that L-amino acids are prepared by fermentation from strains of coryneform bacteria, in particular *Corynebacterium glutamicum*. Prior to the present invention there were no processes for the preparation of nicotinic acid or nicotinic acid derivatives using coryneform bacteria.

SUMMARY OF THE INVENTION

The inventors had the object of providing processes for the fermentative preparation of nicotinic acid and nicotinic acid derivatives.

Accordingly, one object of the present invention is an isolated polynucleotide which encodes a protein comprising the amino acid sequence of SEQ ID NO:2.

Another object of the present invention is the nucleotide sequence of SEQ ID NO:1.

Another object of the present invention are isolated polynucleotides which are complimentary to SEQ ID NO:1 or a 70%, 80% or 90% identical to SEQ ID NO:1.

Another object of the present invention are isolated polynucleotides which hybridizes under stringent conditions to SEQ ID NO:1.

Another object of the present invention are polynucleotides which comprises at least 15 consecutive nucleotides of SEQ ID NO:1.

Another object of the present invention are vectors and host cells containing the polynucleotides. In a preferred embodiment the host cells are Corynebacterium and are preferably *Corynebacterium glutamicum*.

Another object of the present invention is a Coryneform bacterium which has an enhanced nadA gene.

Another object of the present invention is to a process for producing nicotinic acid or a nicotinic acid derivative culturing a host cell in accordance with the invention in a medium suitable for the expression of the polynucleotide; and collecting the nicotinic acid or nicotinic acid derivative. In a preferred embodiment, the nicotinic acid or nicotinic acid derivative is concentrated after it is collected. In another embodiment, the host cell can also contain an pyc, zwa1 and/or prs whose expression is enhanced; and/or an pck, poxB and zwa2 whose expression is attenuated.

Another object of the present invention is a process for screening for polynucleotides which encode a protein having quinolinate synthetase A activity by hybridizing one or more of the polynucleotides embodied in this application to the polynucleotide to be screened; expressing the polynucleotide to produce a protein; and detecting the presence or absence of quinolinate synthetase A activity in said protein.

DETAILED DESCRIPTION OF THE INVENTION

Figure 1:
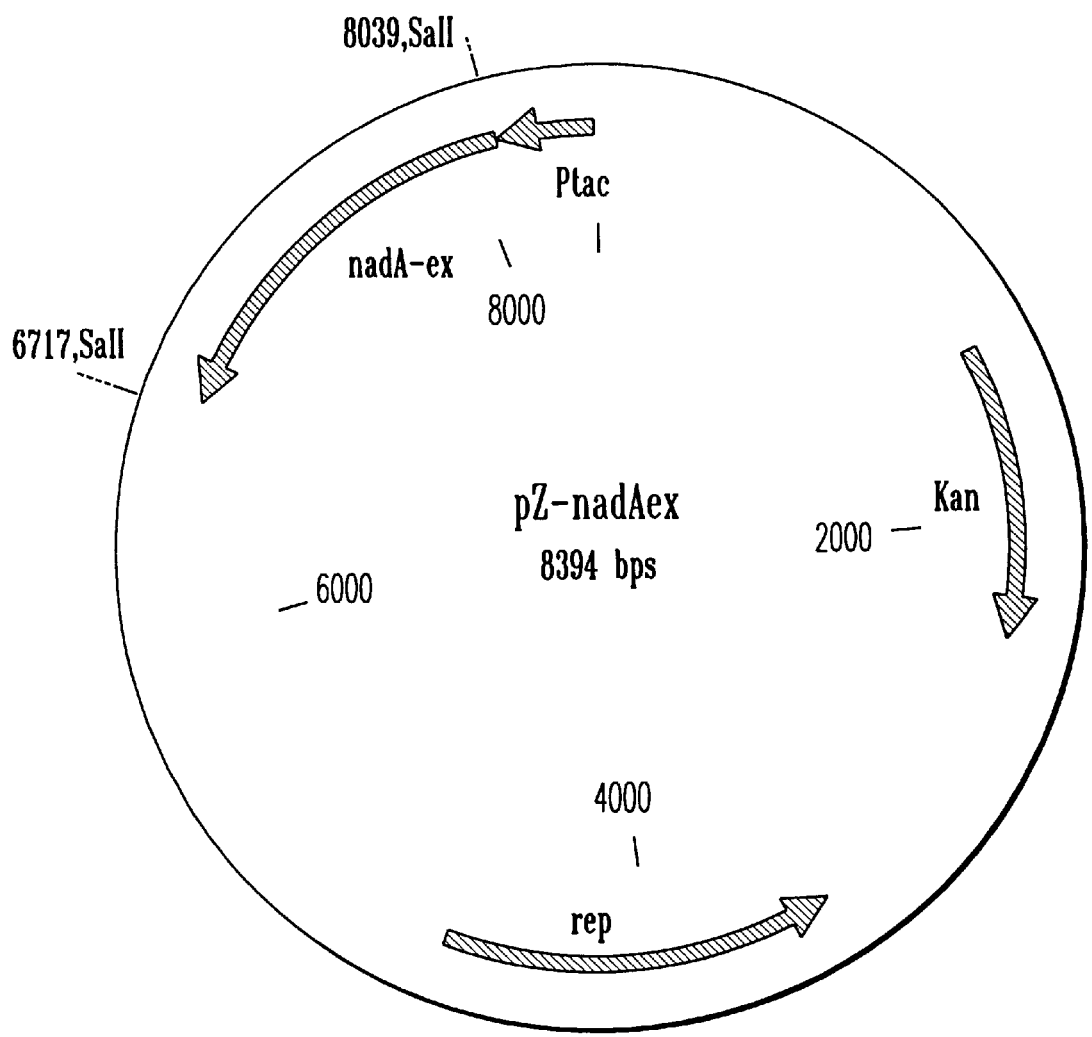
FIG. 1: Map of the plasmid pZ-nadAex

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

"Nicotinic acid or nicotinic acid derivatives" as used herein is understood to mean one or more compounds, including their salts, chosen from nicotinic acid, nicotinamide, quinolinic acid (quinolinate), nicotinic acid mononucleotide, nicotinic acid adenine dinucleotide, nicotinamide adenine dinucleotide (NAD) and nicotinamide adenine dinucleotide phosphate (NADP). Nicotinic acid is particularly preferred.

The invention also provides polynucleotides which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention according to SEQ ID NO:1 or a fragment thereof, and isolation of the polynucleotide sequence mentioned.

Polynucleotides which comprise the sequences according to the invention are suitable as hybridization probes for RNA, cDNA and DNA, in order to isolate, in the full length, nucleic acids or polynucleotides or genes which code for quinolinate synthetase or to isolate those nucleic acids or polynucleotides or genes which have a high similarity with the sequence of the nadA gene. They are also suitable for incorporation into so-called "arrays", micro arrays" or DNA chips" in order to detect and determine the corresponding polynucleotides.

Polynucleotides which comprise the sequences according to the invention are furthermore suitable as primers with the aid of which DNA of genes which code for quinolinate synthetase A can be prepared by the polymerase chain reaction (PCR). Such polynucleotides or oligonucleotides which serve as probes or primers comprise at least 25, 26, 27, 28, 29 or 30, preferably at least 20, 21, 22, 23 or 24, most particularly preferably at least 15, 16, 17, 18 or 19 successive nucleotides. Oligonucleotides with a length of at least 31, 32, 33, 34, 35, 36, 37, 38, 39 or 40, or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" means separated out of its natural environment.

As used herein "Ptac" is understood to meant Ptac promoter; "rep" is understood to mean plasmid-coded replication region from *C. glutamicum* plasmid pGA1; "rrnB" is understood to mean terminator T1T2 of the rrnB gene of *E. coli;* "Kan" is understood to mean a resistance gene for kanamycin; "nadA-ex" is understood to mean nadA gene of *C. glutamicum* without promoter region; and "SalI" is understood to mean a cleavage site of the restriction enzyme SalI.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID NO: 1 or a fragment prepared therefrom and also those which are at least 70% to 80%, preferably at least 81% to 85%, particularly preferably at least 86% to 90%, and most particularly preferably at least 91%, 93%, 95%, 97% or 99% identical to the polynucleotide according to SEQ ID NO: 1 or a fragment prepared therefrom.

"Polypeptides" are understood as meaning peptides or proteins which comprise two or more amino acids bonded via peptide bonds.

The polypeptides according to the invention include a polypeptide according to SEQ ID NO: 2, in particular those with the biological activity of quinolinate synthetase A, and also those which are at least 70% to 80%, preferably at least 81% to 85%, particularly preferably at least 86% to 90%, and most particularly preferably at least 91%, 93%, 95%, 97% or 99% identical to the polypeptide according to SEQ ID NO: 2 and have the activity mentioned.

The invention also relates to a process for the fermentative preparation of nicotinic acid or nicotinic acid derivatives chosen from the group consisting of nicotinic acid, nicotinamide, quinolinic acid (quinolinate), nicotinic acid mononucleotide, nicotinic acid adenine dinucleotide, nicotinamide adenine dinucleotide (NAD) and nicotinamide adenine dinucleotide phosphate (NADP) using coryneform bacteria in which the nucleotide sequences which code for the nadA gene are enhanced, in particular over-expressed.

The term "enhancement" in this connection describes the increase in the intracellular activity of one or more enzymes in a microorganism which are coded by the corresponding DNA, for example by increasing the number of copies of the gene or genes, using a potent promoter or using a gene which codes for a corresponding enzyme having a high activity, and optionally combining these measures.

The microorganisms which the present invention provides can produce nicotinic acid or nicotinic acid derivatives from glucose, sucrose, lactose, fructose, maltose, molasses, starch, cellulose or from glycerol and ethanol. They can be representatives of coryneform bacteria, in particular of the genus Corynebacterium. Of the genus Corynebacterium, there may be mentioned in particular the species *Corynebacterium glutamicum,* which is known among experts for its ability to produce L-amino acids.

Suitable strains of the genus Corynebacterium, in particular of the species *Corynebacterium glutamicum* (*C. glutamicum*), include:

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020.

The isolated nadA gene from *C. glutamicum* codes for the enzyme quinolinate synthetase A.

To isolate the nadA gene or also other genes of *C. glutamicum*, a gene library of this microorganism is first set up in *Escherichia coli* (*E. coli*). Methods of preparing gene libraries are known and described in various textbooks and handbooks. For example, the textbook by Winnacker: Gene und Klone, Eine Einführung in die Gentechnologie [Genes and Clones, An Introduction to Genetic Engineering] (Verlag Chemie, Weinheim, Germany, 1990), or the handbook by Sambrook et al.: Molecular Cloning, A Laboratory Manual (Cold Spring Harbor Laboratory Press, 1989) describe such methods. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences, USA, 84:2160–2164) in the *E. coli* K-12 strain NM554 (Raleigh et al., 1988, Nucleic Acids Research 16:1563–1575). Börmann et al. (Molecular Microbiology 6(3), 317–326) (1992)) in turn describe a gene library of *C. glutamicum* ATCC13032 using the cosmid pHC79 (Hohn and Collins, Gene 11, 291–298 (1980)).

To prepare a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction-and recombination-defective. An example of these is the strain DH5αmcr, which has been described by Grant et al. (Proceedings of the National Academy of Sciences, USA, 87 (1990) 4645–4649). The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977).

The resulting DNA sequences can then be investigated with known algorithms or sequence analysis programs, such as e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)). One or more of these programs may also be used to determine percent homology and/or identity in accordance with the present invention.

The new DNA sequence of *C. glutamicum* which codes for the nadA gene and which, as SEQ ID NO: 1, is a constituent of the present invention has been found. The amino acid sequence of the corresponding protein has furthermore been derived from the present DNA sequence by the methods described above. The resulting amino acid sequence of the nadA gene product is shown in SEQ ID NO: 2. It is known that, during or after translation, enzymes endogenous in the host can split off the N-terminal amino acid methionine or formylmethionine from proteins formed.

Coding DNA sequences which result from SEQ ID NO: 1 by the degeneracy of the genetic code are also a constituent of the invention. In the same way, DNA sequences which hybridize with SEQ ID NO: 1 or parts of SEQ ID NO: 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. Such mutations are also called, inter alia, neutral substitutions. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID NO: 2 are also a constituent of the invention.

In the same way, DNA sequences which hybridize with SEQ ID NO: 1 or parts of SEQ ID NO: 1 are a constituent of the invention. Finally, DNA sequences which are prepared by the polymerase chain reaction (PCR) using primers which result from SEQ ID NO: 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). The hybridization takes place under stringent conditions, that is to say only hybrids in which the probe and target sequence, i. e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approximately 50° C.–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridization, Boehringer Mannheim, Mannheim, Germany, 1995) a temperature of approximately 50° C.–68° C. being established. It is optionally possible to lower the salt concentration to 0.1×SSC. Polynucleotide fragments which are, for example, at least 70% or at least 80% or at least 90% to 95% or at least 96% to 99% identical to the sequence of the probe employed can be isolated by increasing the hybridization temperature stepwise from 50° C. to 68° C. in steps of approximately 1° C.–2° C. It is also possible to isolate polynucleotide fragments which are completely identical to the sequence of the probe employed. Further instructions on hybridization are obtainable on the market in the form of so-called kits (e.g. DIG Easy Hyb from Roche Diagnostics GmbH, Mannheim, Germany, Catalogue NO: 1603558).

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

It has been found that coryneform bacteria produce nicotinic acid in an improved manner after over-expression of the nadA gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative nicotinic acid production. The expression is likewise improved by measures to prolong the life of the mRNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in EP 0 472 869, in U.S. Pat. No. 4,601,893, in Schwarzer and P ühler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in WO 96/15246, in Malumbres et al. (Gene 134, 15–24 (1993)), in JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, for enhancement the nadA gene according to the invention was over-expressed with the aid of episomal plasmids. Suitable plasmids are those which are replicated in coryneform bacteria. Numerous known plasmid vectors, such as e.g. pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as e.g. those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

An example of such a plasmid is the plasmid pZ-nadAex shown in FIG. 1.

Plasmid vectors which are also suitable are also those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schäfer et al., Gene 145, 69–73 (1994)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)), pEM1 (Schrumpf et al, 1991, Journal of Bacteriology 173:4510–4516) or pBGS8 (Spratt et al.,1986, Gene 41:

337–342). The plasmid vector which contains the gene to be amplified is then transferred into the desired strain of *C. glutamicum* by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

In addition, it may be advantageous for the production of nicotinic acid or nicotinic acid derivatives to enhance, in particular over-express, one or more enzymes of glycolysis, of anaplerosis and optionally regulatory proteins, in addition to the nadA gene.

In a preferred embodiment of preparing nicotinic acid or nicotinic acid derivatives, in addition to enhancing the nadA gene, one or more of the following genes can be enhanced:

the pyc gene which codes for pyruvate carboxylase (DE-A-198 31 609), the zwa1 gene which codes for the Zwa1 protein (DE: 199 59 328.0, DSM 13115); and/or the prs gene which codes for phosphoribosyl pyrophosphate synthetase (ACCESSION No.: U76387).

It may also be advantageous for the production of nicotinic acid or nicotinic acid derivatives, to attenuate or reduce the expression of one or more of the following genes:

the pck gene which codes for phosphoenol pyruvate carboxykinase (DE 199 50 409.1; DSM 13047), the poxB gene which codes for pyruvate oxidase (DE: 199 51 975.7; DSM 13114), and/or the zwa2 gene which codes for the Zwa2 protein (DE: 199 59 327.2, DSM 13113).

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

In addition to over-expression of the nadA gene it may furthermore be advantageous, for the production of nicotinic acid or nicotinic acid derivatives, to eliminate undesirable side reactions, (Nakayama: "Breeding of Amino Acid Producing Micro-organisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of nicotinic acid. A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of nicotinic acid or nicotinic acid derivatives are known from the prior art. The concentration of nicotinic acid or nicotinic acid derivatives formed can be determined with microbiological methods, such as, for example, the *Lactobacillus plantarum* test (DIFCO MANUAL, $10^{th}$ Edition, p. 1100–1102; Michigan, USA).

A pure culture of the *C. glutamicum* strain DSM12455/pZ-nadAex was deposited on Oct. 25, 2000 at the Deutsche Sammlung Für Mikroorganismen und Zellkulturen (DSMZ= German Collection of Microorganisms and Cell Cultures, Braunschweig, Germany) in accordance with the Budapest Treaty as DSM13794.

The process according to the invention is used for fermentative preparation of nicotinic acid and nicotinic acid derivatives.

The isolation of plasmid DNA from *Escherichia coli* and all techniques of restriction, Klenow and alkaline phosphatase treatment are carried out by the method of Sambrook et al (Molecular Cloning. A Laboratory Manual (1989) Cold Spring Harbour Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

The strain ATCC13032ΔilvA is deposited as DSM12455 at the Deutsche Sammlung für Mikroorganismen und Zellkulturen in Braunschweig (Germany) in accordance with the Budapest Treaty and is described in EP-A-1006189.

Having generally described this invention, a further understanding can be obtained by reference to certain specific examples which are provided herein for purposes of illustration only, and are not intended to be limiting unless otherwise specified.

EXAMPLES

Example 1
Preparation of a Genomic Cosmid Gene Library from *Corynebacterium Glutamicum* ATCC 13032

Chromosomal DNA from *Corynebacterium glutamicum* ATCC 13032 is isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments are dephosphorylated with shrimp alkaline phosphatase (Roche Diagnostics GmbH, Mannheim, Germany, Product Description SAP, Code no. 1758250). The DNA of the cosmid vector SuperCos1 (Wahl et al. (1987) Proceedings of the National Academy of Sciences, USA 84:2160–2164), obtained from Stratagene (La Jolla, USA, Product Description SuperCos1 Cosmid Vektor Kit, Code no. 251301) is cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA is then cleaved with the restriction enzyme BamHI (Amersham Pharmacia, Freiburg, Germany, Product Description BamHI, Code no. 27-0868-04). The cosmid DNA treated in this manner is mixed with the treated ATCC13032 DNA and the batch is treated with T4 DNA ligase (Amersham Pharmacia, Freiburg, Germany, Product Description T4-DNA-Ligase, Code no. 27-0870-04). The ligation mixture is then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575) the cells are taken up in 10 mM MgSO$_4$ and mixed with an aliquot of the phage suspension. The infection and titering of the cosmid library are carried out as described by Sambrook et al. (1989, Molecular Cloning: A Laboratory Manual, Cold Spring Harbor), the cells being plated out on LB agar (Lennox, 1955, Virology, 1:190) with 100 mg/l ampicillin. After incubation overnight at 37° C., recombinant individual clones are selected.

Example 2
Isolation and Sequencing of the nadA Gene

The cosmid DNA of an individual colony is isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments are dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp is isolated with the QiaExII Gel Extraction Kit (Product No. 20021, Qiagen, Hilden, Germany).

The DNA of the sequencing vector pZero-1, obtained from Invitrogen (Groningen, Holland, Product Description Zero Background Cloning Kit, Product No. K2500-01), is cleaved with the restriction enzyme BamHI (Amersham Pharmacia, Freiburg, Germany, Product Description BamHI, Product No. 27-0868-04). The ligation of the cosmid fragments in the sequencing vector pZero-1 is carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture is then electroporated (Tauch et al. 1994, FEMS Microbiol Letters, 123:343–7) into the *E. coli* strain DH5αMCR (Grant, 1990, Proceedings of the National Academy of Sciences, USA, 87:4645–4649) and plated out on LB agar (Lennox, 1955, Virology, 1:190) with 50 mg/l zeocin.

The plasmid preparation of the recombinant clones is carried out with Biorobot 9600 (Product No. 900200, Qiagen, Hilden, Germany). The sequencing is carried out by the dideoxy chain-stopping method of Sanger et al. (1977, Proceedings of the National Academy of Sciences, USA, 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) is used. The separation by gel electrophoresis and analysis of the sequencing reaction are carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained are then processed using the Staden program package (1986, Nucleic Acids Research, 14:217–231) version 97-0. The individual sequences of the pZero1 derivatives are assembled to a continuous contig. The computer-assisted coding region analysis is prepared with the XNIP program (Staden, 1986, Nucleic Acids Research 14:217–231).

The resulting nucleotide sequence is shown in SEQ ID No. 1. Analysis of the nucleotide sequence shows an open reading frame of 1287 base pairs, which was called the nadA gene. The nadA gene codes for a protein of 428 amino acids.

Example 3
Preparation of the Shuttle Vector pZ-nadAex for Enhancement of the nadA Gene in *C. glutamicum*

3.1. Cloning of the nadA Gene

From the strain ATCC 13032, chromosomal DNA is isolated by the method of Eikmanns et al. (Microbiology 140: 1817–1828 (1994)). On the basis of the sequence of the nadA gene known for *C. glutamicum* from example 2, the following oligonucleotides are chosen for the polymerase chain reaction. In addition, suitable restriction cleavage sites which allow cloning into the target vector are inserted:

```
nadA-ex1 shown in SEQ ID NO:3
5' GAT CTA GTC GAC ATG ACC ACC TCA ATC ACC 3' nadA-ex2 shown in SEQ ID NO:4
5' AAG TCT GTC GAC ACG ATG CGG TCA ATA TGG 3'
```

The primers shown were synthesized by ARK Scientific GmbH Biosystems (Darmstadt, Germany). The primers nadA-ex1 and nadA-ex2 contain the sequence for the cleavage site of the restriction endonuclease SalI, which are marked by underlining in the nucleotide sequences shown above. The PCR reaction is carried out by the standard PCR method of Innis et al. (PCR Protocols. A Guide to Methods and Applications, 1990, Academic Press) with Pwo-Polymerase from Roche Diagnostics GmbH (Mannheim, Germany). With the aid of the polymerase chain reaction, the primers allow amplification of a DNA fragment 1287 bp in size, which carries the nadA gene from *Corynebacterium glutamicum* without a potential promoter region. The fragment amplified in this way is tested electrophoretically in a 0.8% agarose gel and checked by sequencing.

The PCR fragment obtained in this manner is cleaved completely with the restriction enzym SalI and, after separation in a 0.8% agarose gel, isolated from the gel with the QiaExII Gel Extraction Kit (Product No. 20021, Qiagen, Hilden, Germany).

3.2. Cloning of nadA in the Vector pZ8-1

The *E. coli-C. glutamicum* shuttle expression vector pZ8-1 (EP 0 375 889) is employed as the base vector for expression both in *C. glutamicum* and in *E. coli*. DNA of this plasmid is cleaved completely with the restriction enzyme SalI and then dephosphorylated with shrimp alkaline phosphatase (Roche Diagnostics GmbH, Mannheim, Germany, Product Description SAP, Product No. 1758250). The nadA fragment isolated from the agarose gel in example 3.1 is mixed with the vector pZ8-1 prepared in this way and the batch is treated with T4 DNA ligase (Amersham Pharmacia, Freiburg, Germany, Product Description T4-DNA-Ligase, Code no.27-0870-04).

The ligation batch is transformed in the *E. coli* strain DH5αmcr (Hanahan, In: DNA cloning. A Practical Approach, Vol. I, IRL-Press, Oxford, Washington D.C., USA). Selection of plasmid-carrying cells was made by plating out the transformation batch on LB agar (Lennox, 1955, Virology, 1:190) with 50 mg/l kanamycin. After incubation overnight at 37° C., recombinant individual clones are selected. Plasmid DNA is isolated from a transformant with the Qiaprep Spin Miniprep Kit (Product No. 27106, Qiagen, Hilden, Germany) in accordance with the manufacturer's instructions and checked by restriction cleavage. The resulting plasmid is called pZ-nadAex. It is shown in FIG. 1.

Example 4
Transformation of the Strain ATCC13032ΔilvA with the Plasmid pZ-nadAex The strain ATCC13032ΔilvA is transformed with the plasmid pZ-nadAex using the electroporation method described by Liebl et al., (FEMS Microbiology Letters, 53:299–303 (1989)). Selection of the transformants takes place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which has been supplemented with 25 mg/l kanamycin. Incubation is carried out for 2 days at 33° C.

Plasmid DNA is isolated from a transformant by conventional methods (Peters-Wendisch et al., 1998, Microbiology, 144, 915–927), cleaved with the restriction endonuclease SalI, and the plasmid is checked by subsequent agarose gel electrophoresis.

The resulting strain is called *C. glutamicum* ATCC13032ΔilvA/pZ-nadAex or DSM12455/pZnadAex.

Example 5
Preparation of Nicotinic Acid

The formation of nicotinic acid by the *C. glutamicum* strains ATCC13032ΔilvA/pZ8-1 and ATCC13032ΔilvA/pZ-nadAex is tested in medium CGXII (Keilhauer et al, 1993, Journal of Bacteriology, 175:5595–5603), which was supplemented with 25 µg/ml kanamycin and 1 mM L-isoleucine.

This medium is called *C. glutamicum* test medium in the following. In each case 50 ml of freshly prepared *C. glutamicum* test medium are inoculated with a 16 hours old preculture of the same medium such that the optical density of the culture suspension ($OD_{580}$) at the start of incubation is 0.1. The cultures are incubated at 30° C. and 130 rpm. After incubation for 48 hours the optical density ($OD_{580}$) of the culture is determined and the cells are then removed by centrifugation at 5000 g for 10 minutes and the supernatant subjected to sterile filtration.

A Novaspec II photometer from Pharmacia (Freiburg, Germany) is employed at a measurement wavelength of 580 nm for determination of the optical density.

The nicotinic acid in the culture supernatant is quantified by means of *Lactobacillus plantarum* ATCC 8014 in accordance with the instructions in the handbook of DIFCO (DIFCO MANUAL, 10th Edition, p. 1100–1102; Michigan, USA). Nicotinic acid from Sigma (Deisenhofen, Germany) is used for the calibration.

TABLE 2

| Strain | Cell density $OD_{580}$ | Concentration (ng/ml) |
|---|---|---|
| ATCC13032ΔilvA/pZ8-1 | 12 | 24 |
| ATCC13032ΔilvA/pZ-nadAex | 14 | 31 |

The present application claims priority to German Application No. DE10055869.0 filed on Nov. 10, 2000, the entire contents of which are hereby incorporated into the present application by reference.

Obviously, numerous modifications and variations on the present invention are possible in light of the above teachings. It is therefore to be understood that within the scope of the appended claims, the invention may be practised otherwise than as specifically described herein.

What is claimed is:

1. An isolated polynucleotide which encodes a protein comprising the amino acid sequence of SEQ ID NO:2, wherein said protein has quinolinate synthetase activity.

2. An isolated polynucleotide, which comprises SEQ ID NO:1 and encodes a protein having quinolinate synthetase activity.

3. An isolated polynucleotide which is complimentary to the polynucleotide of claim 2.

4. An isolated polynucleotide which hybridizes under stringent conditions to the complement of SEQ ID NO: 1; wherein said stringent conditions comprise washing in 5xSSC at a temperature from 50 to 68° C., and wherein the polynucleotide encodes a protein having quinolinate synthetase activity.

5. A vector comprising the isolated polynucleotide of claim 1.

6. A vector comprising the isolated polynucleotide of claim 2.

7. A host cell comprising the isolated polynucleotide of claim 1.

8. A host cell comprising the isolated polynucleotide of claim 2.

9. The host cell of claim 7, which is a coryneform bacterium.

10. The host cell of claim 8, which is a coryneform bacterium.

11. The host cell of claim 9, which is *Coryneform glutamicum*.

12. The host cell of claim 9, which is *Coryneform glutamicum*.

13. A process for producing nicotinic acid or a nicotinic acid derivative comprising:

culturing the host cell of claim 7 in a medium suitable for the expression of the polynucleotide; and collecting the nicotinic acid or nicotinic acid derivative.

14. The process of claim 13, wherein after said collecting the process further comprises a step of concentrating the nicotinic acid or nicotinic acid derivative.

15. The process of claim 13, wherein the host cell further comprises at least one gene whose expression is enhanced, wherein said gene is selected from the group consisting of pyc, zwa1 and prs.

16. The process of claim 15, wherein the enhanced expression of said gene comprises overexpression of the gene.

17. The process of claim 13, wherein the host cell further comprises at least one gene whose expression is attenuated, wherein said gene is selected from the group consisting of pck, poxB and zwa2.

18. A process for producing nicotinic acid or a nicotinic acid derivative comprising:

culturing the host cell of claim 8 in a medium suitable for the expression of the polynucleotide; and collecting the nicotinic acid or nicotinic acid derivative.

19. The process of claim 18, wherein after said collecting the process further comprises a step of concentrating the nicotinic acid or nicotinic acid derivative.

20. The process of claim 18, wherein the host cell further comprises at least one gene whose expression is enhanced, wherein said gene is selected from the group consisting of pyc, zwa1 and prs.

21. The process of claim 20, wherein the enhanced expression of said gene comprises overexpression of the gene.

22. The process of claim 18, wherein the host cell further comprises at least one gene whose expression is attenuated, wherein said gene is selected from the group consisting of pck, poxB and zwa2.

23. A An isolated polynucleotide which comprises at least 30 consecutive nucleotides of the polynucleotide of claim 2.

* * * * *

SEQUENCE LISTING

```
<160> NUMBER OF SEQ ID NOS: 4

<210> SEQ ID NO 1
<211> LENGTH: 2730
<212> TYPE: DNA
<213> ORGANISM: Corynebacterium glutamicum
<220> FEATURE:
<221> NAME/KEY: CDS
<222> LOCATION: (743)..(2026)
```

-continued

<223> OTHER INFORMATION: nadA gene

<400> SEQUENCE: 1

```
ctgtaagata gctcaacagt taaagtcaga ttgaccctaa ggtggtttct tgcccgcttc      60
acctgaaatc cagatggccg tatccacgat catcttcgcg ctgcgcccg gcccccagga    120
tctccccagc ctgtgggccc ccttcgttcc gcgcacccgc gaaccacatt taaataaatg    180
ggcactgccc ggcggttggc tgccaccaca tgaagaactt gaagatgctg ctgcccgcac    240
actcgcagaa accaccggcc tgcaccccag ctatctagaa cagctctaca ctttcggaaa    300
agtcgaccgc tccccaaccg gacgcgtgat ctctgtggtg tattgggcac ttgtccgagc    360
cgatgaagcg ttgaaagcca tcccaggaga aaacgtccag tggtttcccg ccgatcatct    420
ccctgagctg gcatttgacc acaataacat cgtcaaatat gcactagaac gacttcgcac    480
caaggtggaa tactccgaaa tcgcccactc cttcctcgga gaaaccttca ccatcgccca    540
gcttcgatcc gtgcatgagg cagtccttgg acacaaactc gatgccgcca acttccgaag    600
atccgtggcc acctcgcccg atctgatcga caccggcgaa gtgcttgcgg aacaccgca    660
ccgcccaccc aaactgttca gattccaaag ataaattctg acgctcattc cagcccaccg    720
tttagaagaa aagaccccaa tc atg acc acc tca atc acc cca tct gtc aac      772
                        Met Thr Thr Ser Ile Thr Pro Ser Val Asn
                        1               5                   10 ctt gca ttg aaa aat gcc aat agc tgc aac agt gaa ctc aaa gac gga     820
Leu Ala Leu Lys Asn Ala Asn Ser Cys Asn Ser Glu Leu Lys Asp Gly
                15                  20                  25 ccc tgg ttc ctc gac cag ccc gga atg ccg gat gtc tac ggc ccc ggc     868
Pro Trp Phe Leu Asp Gln Pro Gly Met Pro Asp Val Tyr Gly Pro Gly
        30                  35                  40 gcg tca caa aac gat ccg atc cct gcg cat gct ccg cgc cag cag gtt     916
Ala Ser Gln Asn Asp Pro Ile Pro Ala His Ala Pro Arg Gln Gln Val
    45                  50                  55 ctc ccc gag gag tac cag cgc gca agt gat gac gaa ctg cat cgt agg     964
Leu Pro Glu Glu Tyr Gln Arg Ala Ser Asp Asp Glu Leu His Arg Arg
60                  65                  70 atc cgg gaa gcg aaa gac acc ctg ggt gac aaa gtg gtt atc cta gga    1012
Ile Arg Glu Ala Lys Asp Thr Leu Gly Asp Lys Val Val Ile Leu Gly
75                  80                  85                  90 cac ttc tac cag cgc gat gaa gtt atc caa cac gca gat ttt gtt ggt    1060
His Phe Tyr Gln Arg Asp Glu Val Ile Gln His Ala Asp Phe Val Gly
                95                  100                 105 gac tct ttc caa ctt gcc cgc gct gcc aaa acc cga ccc gag gcg gaa    1108
Asp Ser Phe Gln Leu Ala Arg Ala Ala Lys Thr Arg Pro Glu Ala Glu
        110                 115                 120 gcg att gtg ttc tgc ggt gtg cac ttc atg gct gaa acc gct gat ctg    1156
Ala Ile Val Phe Cys Gly Val His Phe Met Ala Glu Thr Ala Asp Leu
    125                 130                 135 tta tcc acg gat gaa caa tca gtg atc ctc ccc aac ctt gcc gca ggt    1204
Leu Ser Thr Asp Glu Gln Ser Val Ile Leu Pro Asn Leu Ala Ala Gly
    140                 145                 150 tgc tcc atg gca gac atg gct gac ctt gat tcc gtc gaa gac tgc tgg    1252
Cys Ser Met Ala Asp Met Ala Asp Leu Asp Ser Val Glu Asp Cys Trp
155                 160                 165                 170 gag caa ctc acc tca att tat ggc gat gac acc ctg atc cct gtg acc    1300
Glu Gln Leu Thr Ser Ile Tyr Gly Asp Asp Thr Leu Ile Pro Val Thr
                175                 180                 185 tac atg aat tcc tct gca gcg ctc aaa ggt ttc gtg ggt gag cac ggc    1348
Tyr Met Asn Ser Ser Ala Ala Leu Lys Gly Phe Val Gly Glu His Gly
        190                 195                 200
```

-continued

```
gga att gta tgc acc tcc tca aat gca cgt tcc gta ttg gag tgg gcg      1396
Gly Ile Val Cys Thr Ser Ser Asn Ala Arg Ser Val Leu Glu Trp Ala
        205                 210                 215 ttt gaa cgc ggc caa cga gtc ctg ttc ttc ccc gat cag cac ttg ggt      1444
Phe Glu Arg Gly Gln Arg Val Leu Phe Phe Pro Asp Gln His Leu Gly
220                 225                 230 cga aac acc gcg aaa gcc atg ggc att ggg atc gat caa atg ccc ctg      1492
Arg Asn Thr Ala Lys Ala Met Gly Ile Gly Ile Asp Gln Met Pro Leu
235                 240                 245                 250 tgg aat ccc aac aaa cca ctg ggt ggc aac acc gtt tcc gag cta gaa      1540
Trp Asn Pro Asn Lys Pro Leu Gly Gly Asn Thr Val Ser Glu Leu Glu
                255                 260                 265 aac gca aag gta ctg ctc tgg cat ggt ttc tgc tct gta cac aag cgc      1588
Asn Ala Lys Val Leu Leu Trp His Gly Phe Cys Ser Val His Lys Arg
            270                 275                 280 ttt act gtc gag cag atc aac aaa gcc cgc gcc gag tac ccc gac gtt      1636
Phe Thr Val Glu Gln Ile Asn Lys Ala Arg Ala Glu Tyr Pro Asp Val
        285                 290                 295 cac gtc atc gtg cac cct gaa tcc ccc atg cca gtt gtt gac gcc gcc      1684
His Val Ile Val His Pro Glu Ser Pro Met Pro Val Val Asp Ala Ala
300                 305                 310 gac tca tcc gga tcc act gac ttc att gtg aaa gcc att caa gca gca      1732
Asp Ser Ser Gly Ser Thr Asp Phe Ile Val Lys Ala Ile Gln Ala Ala
315                 320                 325                 330 ccg gca gga tct acc ttt gcg atc ggc acc gaa atc aac ttg gtt cag      1780
Pro Ala Gly Ser Thr Phe Ala Ile Gly Thr Glu Ile Asn Leu Val Gln
                335                 340                 345 cgc ctg gca gcc cag tac ccg cag cac acc atc ttc tgc ctc gac cct      1828
Arg Leu Ala Ala Gln Tyr Pro Gln His Thr Ile Phe Cys Leu Asp Pro
            350                 355                 360 gtc atc tgc cca tgc tcc acc atg tat cgc att cac cct ggt tac ctg      1876
Val Ile Cys Pro Cys Ser Thr Met Tyr Arg Ile His Pro Gly Tyr Leu
        365                 370                 375 gcc tgg gca ctt gag gag ttg gtg gct gga aac gtg att aac cag att      1924
Ala Trp Ala Leu Glu Glu Leu Val Ala Gly Asn Val Ile Asn Gln Ile
380                 385                 390 tct gtc tct gaa tcc gtg gcg gca ccg gcg cga gtc gct ttg gaa agg      1972
Ser Val Ser Glu Ser Val Ala Ala Pro Ala Arg Val Ala Leu Glu Arg
395                 400                 405                 410 atg cta tct gtt gtt cca gca gct cct gtt act cct agc tcc tcg aag      2020
Met Leu Ser Val Val Pro Ala Ala Pro Val Thr Pro Ser Ser Ser Lys
                415                 420                 425 gat gcg taatttatga ctacccatat tgaccgcatc gttggcgcag cgttatccga       2076
Asp Ala ggatgcgcca tggggcgaca ttacctccga cactttatc ccaggatcgg cgcagctgag    2136
cgccaaggtt gttgcccggg agccaggtgt gttcagcggg caggcgcttt tcgacgcctc    2196
cttccggctc gtcgatccta ggataaacgc atcccttaag gtggctgatg gtgacagctt    2256
tgaaaccggg gacatcctag aacaattac cggcagtgct agaagcatcc tccgttcaga    2316
gcgcattgct ctcaacttca ttcagaggac gtccggcatc gctacattga catcgtgcta    2376
tgttgcagag gttaaaggca ccaaagcccg cattgttgat acccggaaaa ccacacccgg    2436
cctgcgcatc attgaacgcc aagctgtccg tgacggtggc ggatttaatc accgagccac    2496
cttgtccgat gctgtcatgg tgaaagataa ccatctcgca gccatcgcat cccaggggct    2556
cagcatcact gaagcgctgt cgaatatgaa agctaaactc ccccacacca cccatgtgga    2616
agtcgaagtt gatcatatag agcagatcga accagttctt gctgctggtg tggacaccat    2676
```

```
catgttggat aatttcacca ttgatcagct catcgaaggc gttgatctca ttgg         2730
```

<210> SEQ ID NO 2
<211> LENGTH: 428
<212> TYPE: PRT
<213> ORGANISM: Corynebacterium glutamicum

<400> SEQUENCE: 2

```
Met Thr Thr Ser Ile Thr Pro Ser Val Asn Leu Ala Leu Lys Asn Ala
 1               5                  10                  15

Asn Ser Cys Asn Ser Glu Leu Lys Asp Gly Pro Trp Phe Leu Asp Gln
            20                  25                  30

Pro Gly Met Pro Asp Val Tyr Gly Pro Gly Ala Ser Gln Asn Asp Pro
        35                  40                  45

Ile Pro Ala His Ala Pro Arg Gln Gln Val Leu Pro Glu Glu Tyr Gln
    50                  55                  60

Arg Ala Ser Asp Asp Glu Leu His Arg Arg Ile Arg Glu Ala Lys Asp
65                  70                  75                  80

Thr Leu Gly Asp Lys Val Val Ile Leu Gly His Phe Tyr Gln Arg Asp
                85                  90                  95

Glu Val Ile Gln His Ala Asp Phe Val Gly Asp Ser Phe Gln Leu Ala
            100                 105                 110

Arg Ala Ala Lys Thr Arg Pro Glu Ala Glu Ala Ile Val Phe Cys Gly
        115                 120                 125

Val His Phe Met Ala Glu Thr Ala Asp Leu Leu Ser Thr Asp Glu Gln
    130                 135                 140

Ser Val Ile Leu Pro Asn Leu Ala Gly Cys Ser Met Ala Asp Met
145                 150                 155                 160

Ala Asp Leu Asp Ser Val Glu Asp Cys Trp Glu Gln Leu Thr Ser Ile
                165                 170                 175

Tyr Gly Asp Asp Thr Leu Ile Pro Val Thr Tyr Met Asn Ser Ser Ala
            180                 185                 190

Ala Leu Lys Gly Phe Val Gly His Gly Gly Ile Val Cys Thr Ser
        195                 200                 205

Ser Asn Ala Arg Ser Val Leu Glu Trp Ala Phe Glu Arg Gly Gln Arg
    210                 215                 220

Val Leu Phe Phe Pro Asp Gln His Leu Gly Arg Asn Thr Ala Lys Ala
225                 230                 235                 240

Met Gly Ile Gly Ile Asp Gln Met Pro Leu Trp Asn Pro Asn Lys Pro
                245                 250                 255

Leu Gly Gly Asn Thr Val Ser Glu Leu Glu Asn Ala Lys Val Leu Leu
            260                 265                 270

Trp His Gly Phe Cys Ser Val His Lys Arg Phe Thr Val Glu Gln Ile
        275                 280                 285

Asn Lys Ala Arg Ala Glu Tyr Pro Asp Val His Val Ile Val His Pro
    290                 295                 300

Glu Ser Pro Met Pro Val Val Asp Ala Ala Asp Ser Ser Gly Ser Thr
305                 310                 315                 320

Asp Phe Ile Val Lys Ala Ile Gln Ala Ala Pro Ala Gly Ser Thr Phe
                325                 330                 335

Ala Ile Gly Thr Glu Ile Asn Leu Val Gln Arg Leu Ala Ala Gln Tyr
            340                 345                 350

Pro Gln His Thr Ile Phe Cys Leu Asp Pro Val Ile Cys Pro Cys Ser
        355                 360                 365
```

```
Thr Met Tyr Arg Ile His Pro Gly Tyr Leu Ala Trp Ala Leu Glu Glu
    370                 375                 380

Leu Val Ala Gly Asn Val Ile Asn Gln Ile Ser Val Ser Glu Ser Val
385                 390                 395                 400

Ala Ala Pro Ala Arg Val Ala Leu Glu Arg Met Leu Ser Val Val Pro
                405                 410                 415

Ala Ala Pro Val Thr Pro Ser Ser Ser Lys Asp Ala
            420                 425

<210> SEQ ID NO 3
<211> LENGTH: 30
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA; primer nadA-ex

<400> SEQUENCE: 3
gatctagtcg acatgaccac ctcaatcacc                                    30

<210> SEQ ID NO 4
<211> LENGTH: 30
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA; primer nadA-ex

<400> SEQUENCE: 4
aagtctgtcg acacgatgcg gtcaatatgg                                    30
```